US00PP19319P2

(12) United States Plant Patent
Hop

(10) Patent No.: US PP19,319 P2
(45) Date of Patent: Oct. 14, 2008

(54) ***PIERIS* PLANT NAMED 'PASSION'**

(50) Latin Name: *Pieris japonica*
Varietal Denomination: Passion

(76) Inventor: Margareth E. C. M. Hop, P.O. Box 85, 2160 AB, Lisse (NL)

( * ) Notice: Subject to any disclaimer, the term of this patent is extended or adjusted under 35 U.S.C. 154(b) by 0 days.

(21) Appl. No.: 11/974,219

(22) Filed: Oct. 11, 2007

(51) Int. Cl.
*A01H 5/00* (2006.01)

(52) U.S. Cl. ..... Plt./226
(58) Field of Classification Search ..... Plt./226
See application file for complete search history.

(56) References Cited

PUBLICATIONS

UPOV–ROM search for PBR 20052636 for cultivar Passion p. 1.*

* cited by examiner

*Primary Examiner*—Annette H Para
(74) *Attorney, Agent, or Firm*—C. A. Whealy

(57) ABSTRACT

A new and distinct cultivar of *Pieris* plant named 'Passion', characterized by its upright and outwardly spreading plant habit; freely branching habit; large inflorescences with numerous red purple-colored flowers; developing inflorescences upright; and good garden performance.

2 Drawing Sheets

Botanical designation: *Pieris japonica.*
Cultivar denomination: 'Passion'.

BACKGROUND OF THE INVENTION

The present Invention relates to a new and distinct cultivar of *Pieris,* botanically known as *Pieris japonica,* and hereinafter referred to by the name 'Passion'.

The new *Pieris* is a product of a planned breeding program conducted by the Inventor in Boskoop, The Netherlands. The objective of the breeding program is to create new *Pieris* varieties having upright inflorescences and attractive flower color.

The new *Pieris* originated from a cross-pollination made by the Inventor in March, 1988, in Boskoop, The Netherlands, of an unnamed seedling selection of *Pieris japonica,* not patented, as the female, or seed, parent with the *Pieris japonica* cultivar Valley Valentine, not patented, as the male, or pollen, parent. The new *Pieris* was discovered and selected by the Inventor as a flowering plant within the progeny of the stated cross-pollination in a controlled environment in Boskoop, The Netherlands in March 1999.

Asexual reproduction of the new *Pieris* by cuttings taken in a controlled environment in Boskoop, The Netherlands since 2000 has shown that the unique features of this new *Pieris* are stable and reproduced true to type in successive generations.

SUMMARY OF THE INVENTION

The new *Pieris* has not been observed under all possible environmental conditions. The phenotype may vary somewhat with variations in environment such as temperature and/or light intensity without, however, any variance in genotype. The following traits have been repeatedly observed and are determined to be the unique characteristics of 'Passion'. These characteristics in combination distinguish 'Passion' as a new and distinct cultivar of *Pieris:*

1. Upright and outwardly spreading plant habit.
2. Freely branching habit.
3. Large inflorescences with numerous red purple-colored flowers.
4. Developing inflorescences upright.
5. Good garden performance.

Plants of the new *Pieris* differ from plants of the female parent selection primarily in flower color as plants of the female parent selection have white-colored flowers.

Plants of the new *Pieris* differ from plants of the male parent, the cultivar Valley Valentine, in the following characteristics:

1. Plants of the new *Pieris* develop roots more easily than plants of the cultivar Valley Valentine.
2. Plants of the new *Pieris* are more freely branching than plants of the cultivar Valley Valentine.
3. Inflorescences of plants of the new *Pieris* are more upright than inflorescences of plants of the cultivar Valley Valentine.

Plants of the new *Pieris* can be compared to the plants of the *Pieris* cultivar Rosalinda, not patented. In side-by-side comparisons conducted in Boskoop, The Netherlands, plants of the new *Pieris* differed from plants of the cultivar Rosalinda in the following characteristics:

1. Developing leaves of plants of the new *Pieris* were light green in color whereas developing leaves of plants of the cultivar Rosalinda were brownish red in color.
2. Flowers of plants of the new *Pieris* were red purple in color whereas flowers of plants of the cultivar Rosalinda were light pink in color.

BRIEF DESCRIPTION OF THE PHOTOGRAPHS

The accompanying colored photographs illustrate the overall appearance of the *Pieris.* These photographs show the colors as true as it is reasonably possible to obtain in colored reproductions of this describe the colors of the new *Pieris.*

The photograph on the first sheet comprises a side perspective view of a typical flowering plant of 'Passion' grown in a container.

The photograph at the top of the second sheet is a close-up view of a typical leaf of 'Passion'.

The photograph at the bottom of the second sheet is a close-up view of typical flowering stems of 'Passion'.

DETAILED BOTANICAL DESCRIPTION

The aforementioned photographs and following observations and measurements describe plants grown in Boskoop, The Netherlands in 17-cm containers, in a glass-covered greenhouse during the winter and under commercial production conditions. During the production of the plants, day temperatures ranged from 7° C. to 16° C. and night temperatures ranged from 2° C. to 10° C. Plants used for the photographs and description were about four years old. In the following description, color references are made to The Royal Horticultural Society Colour Chart, 2001 Edition, except where general terms of ordinary dictionary significance are used.

Botanical classification: *Pieris japonica* 'Passion'.

Parentage:

*Female, or seed, parent.*—Unnamed seedling selection of *Pieris japonica,* not patented.

*Male, or pollen, parent.*—*Pieris japonica* cultivar Valley Valentine, not patented.

Propagation:

*Type.*—By cuttings.

*Time to initiate roots, winter.*—About ten weeks at temperatures of 18° C.

*Root description.*—Fine, fibrous; light brown in color.

*Rooting habit.*—Moderate branching; moderately dense.

Plant description:

*Plant form and growth habit.*—Perennial, evergreen; upright and outwardly spreading plant habit; broad inverted triangle. Moderately vigorous growth habit.

*Branching habit.*—Freely branching habit; about six lateral branches develop per plant.

*Plant height, soil level to top of flowers.*—About 31 cm.

*Plant diameter, area of spread.*—About 21.2 cm.

*Lateral branch description.*—Length: About 10.1 cm. Diameter: About 3 mm. Internode length: About 3 mm to 7 mm. Strength: Strong. Texture: Smooth, glabrous. Color: 143A.

*Foliage description.*—Arrangement: Alternate or whorled at terminals; simple. Length: About 5 cm. Width: About 1.7 cm. Shape: Oblanceolate. Apex: Acute. Base: Attenuate. Margin: Crenate. Venation pattern: Pinnate. Texture, upper and lower surfaces: Smooth, glabrous. Color: Developing foliage, upper and lower surfaces: 144A. Fully expanded foliage, upper surface: Between 137A and 147A; venation, 143C. Fully expanded foliage, lower surface: Between 143A and 144A; venation, 144B. Petiole: Length: About 9 mm. Diameter: About 1 mm. Texture, upper and lower surfaces: Smooth, glabrous. Color, upper and lower surfaces: 144B.

Flower description:

*Flower arrangement and appearance.*—Single urceolate flowers arranged on terminal paniculate racemes. Developing inflorescences initially upright then bending with the weight of developing flowers. Freely flowering habit; about 135 flowers develop per inflorescence during the flowering period.

*Natural flowering season.*—Plants of the new *Pieris* typically flower in March in The Netherlands. Flowers not persistent.

*Flower longevity.*—Individual flowers last about two weeks on the plant.

*Fragrance.*—Sweet, pleasant.

*Inflorescence length.*—About 7.5 cm.

*Inflorescence diameter.*—About 10.4 cm.

*Flower diameter.*—About 7 mm.

*Flower depth.*—About 7 cm.

*Flower bud.*—Length: About 6 mm. Diameter: About 4 mm. Shape: Ovoid. Color: 187C; towards the apex, 187A.

*Petals.*—Arrangement: Single urceolate flower form; single whorl of five petals fused at the base. Length: About 7 mm. Width: About 2 mm. Shape: Roughly ovate with obtuse apex. Margin: Entire. Texture, upper and lower surfaces: Smooth, glabrous. Color: When opening, upper surface: 185C; towards the base, 155A. When opening, lower surface: 59B; towards the base, 155C. Fully opened, upper surface: 185C to 185D; towards the base, 155A. Fully opened, lower surface: 60B; color becoming closer to 60C to 60D with development; towards the base, 155C.

*Sepals.*—Arrangement: Five fused in a single whorl. Length: About 3 mm. Width: About 1 mm. Shape: Ovate. Apex: Acute. Base: Broadly cuneate. Texture, upper and lower surfaces: Smooth, glabrous. Color: Immature, upper and lower surfaces: 187A. Mature, lower surface: 145C to 145D.

*Peduncles.*—Length: About 9.1 cm. Diameter: About 1.5 mm. Angle: Initially upright to about 80° from vertical. Strength: Moderately strong. Texture: Smooth, glabrous. Color: 200C.

*Pedicels.*—Length: About 4.5 mm. Diameter: Less than 1 mm. Angle: About 50° from vertical. Strength: Moderately strong. Texture: Smooth, glabrous. Color: 183A to 183B.

*Reproductive organs.*—Androecium: Quantity per flower: About ten. Anther shape: Roughly oval. Anther length: About 1 mm. Anther color: 200A. Pollen amount: Scarce. Pollen color: Close to N167C. Gynoecium: Quantity of pistils per flower: Typically one. Pistil length: About 5 mm. Style length: About 4.5 mm. Style color: 145D. Stigma shape: Narrowly club-shaped. Stigma diameter: Less than 1 mm. Stigma color: Close to 144B. Ovary color: 143A.

*Seed/fruit.*—Seed and fruit development have not been observed.

Garden performance: Plants of the new *Pieris* have been observed to have good garden performance and to be tolerant to rain and wind and temperatures from about −15° C. to about 33° C.

Disease/pest resistance: Plants have not been observed to be resistant to pathogens and pests common to *Pieris*.

It is claimed:

1. A new and distinct cultivar of *Pieris* plant named 'Passion' as illustrated and described.

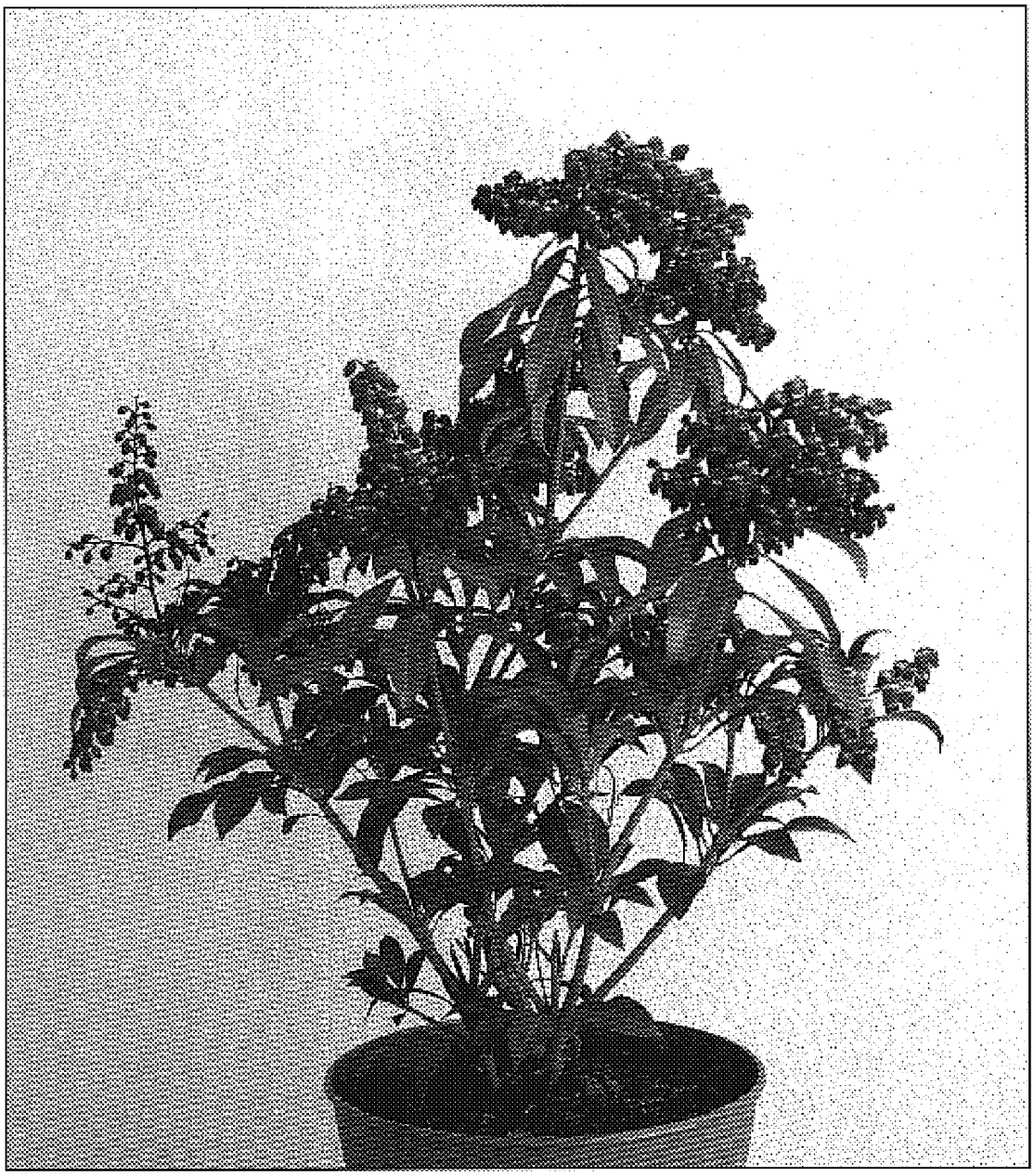

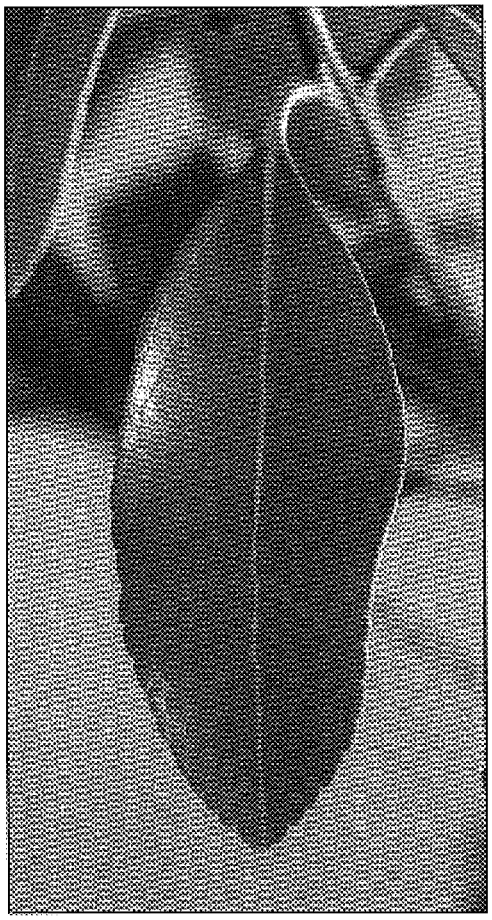
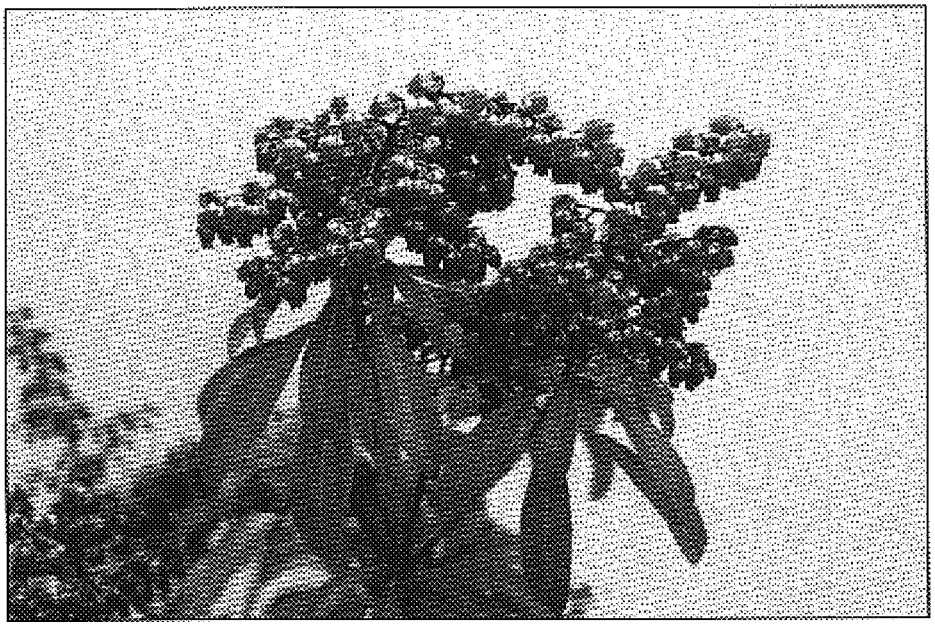

* * * * *